(12) United States Patent
Skinner

(10) Patent No.: US 11,020,161 B2
(45) Date of Patent: Jun. 1, 2021

(54) TACTILE CERCLAGE WIRE AND CABLE PASSER AND METHODS OF USE

(71) Applicant: Harry B. Skinner, Corona Del Mar, CA (US)

(72) Inventor: Harry B. Skinner, Corona Del Mar, CA (US)

(*) Notice: Subject to any disclaimer, the term of this patent is extended or adjusted under 35 U.S.C. 154(b) by 141 days.

(21) Appl. No.: 16/333,492

(22) PCT Filed: Sep. 15, 2017

(86) PCT No.: PCT/US2017/051910
§ 371 (c)(1),
(2) Date: Mar. 14, 2019

(87) PCT Pub. No.: WO2018/053351
PCT Pub. Date: Mar. 22, 2018

(65) Prior Publication Data
US 2019/0254728 A1    Aug. 22, 2019

Related U.S. Application Data

(60) Provisional application No. 62/396,197, filed on Sep. 18, 2016.

(51) Int. Cl.
*A61B 17/88* (2006.01)
*A61B 17/82* (2006.01)
*A61B 17/56* (2006.01)
*A61B 17/00* (2006.01)
*A61B 17/90* (2006.01)

(52) U.S. Cl.
CPC .......... *A61B 17/8861* (2013.01); *A61B 17/56* (2013.01); *A61B 17/82* (2013.01); *A61B 2017/00424* (2013.01); *A61B 2017/00438* (2013.01); *A61B 2017/90* (2013.01)

(58) Field of Classification Search
CPC ..... A61B 17/8861; A61B 17/56; A61B 17/82; A61B 2017/00424; A61B 2017/00438; A61B 2017/90
USPC .................................................. 606/103, 139
See application file for complete search history.

(56) References Cited

U.S. PATENT DOCUMENTS

| | | | | |
|---|---|---|---|---|
| 1,174,887 A | * | 3/1916 | Meriwether | A61F 13/105 294/25 |
| 2,668,536 A | * | 2/1954 | Farries | A61B 17/32 606/167 |
| 4,892,520 A | * | 1/1990 | Gilbaugh | A61B 10/0241 604/117 |

(Continued)

OTHER PUBLICATIONS

International Search Report for PCT/US2017/051910 dated Dec. 14, 2017 in 8 pages.

*Primary Examiner* — Eduardo C Robert
*Assistant Examiner* — David C Comstock
(74) *Attorney, Agent, or Firm* — Nguyen Tarbet LLC

(57) ABSTRACT

A surgical device is disclosed which provides a safe means of passing a cerclage wire around a bone and the technique for accomplishing this task is described. This device uses the tactile sensation of the human hand to achieve appropriate placement of the cerclage wire. Thus, Irregularities in the bone fragments of a fracture or bone graft augmenting a fracture can safely be encircled and secured. The device permits retrograde placement of the cerclage wire compatible with available manufactured devices.

21 Claims, 7 Drawing Sheets

(56) References Cited

U.S. PATENT DOCUMENTS

| | | | |
|---|---|---|---|
| 4,991,592 A * | 2/1991 | Christ | A61B 42/10 |
| | | | 600/567 |
| 5,417,690 A | 5/1995 | Sennett et al. | |
| 5,507,041 A | 4/1996 | Wright | |
| 6,605,091 B1 | 8/2003 | Iwanski | |
| 8,257,366 B2 | 9/2012 | Schneider et al. | |
| 8,333,767 B2 | 12/2012 | Dorf | |
| 8,758,371 B2 * | 6/2014 | Gaynor | A61B 17/0401 |
| | | | 606/148 |
| 9,241,722 B2 | 1/2016 | Yu | |
| 9,439,698 B2 | 9/2016 | Songer et al. | |
| 9,486,563 B2 * | 11/2016 | Taddeo | A61C 17/04 |
| 2004/0193211 A1 * | 9/2004 | Voegele | A61B 5/6838 |
| | | | 606/205 |
| 2008/0243178 A1 | 10/2008 | Oren et al. | |
| 2008/0311543 A1 * | 12/2008 | Viscomi | A61C 19/006 |
| | | | 433/163 |
| 2012/0123410 A1 * | 5/2012 | Craig | A61B 18/14 |
| | | | 606/41 |
| 2014/0012292 A1 * | 1/2014 | Stewart | A61B 17/0485 |
| | | | 606/148 |
| 2016/0235461 A1 * | 8/2016 | Sumko | A61B 17/8897 |
| 2017/0172486 A1 * | 6/2017 | George | G02B 6/3893 |
| 2017/0196671 A1 * | 7/2017 | Harari | A61B 17/0401 |

* cited by examiner

TACTILE CERCLAGE WIRE AND CABLE PASSER AND METHODS OF USE

PRIORITY CLAIM

This application is the U.S. National Phase under 35 U.S.C. § 371 of International Application No. PCT/US2017/051910, filed Sep. 15, 2017, which claims the benefit as a nonprovisional application of U.S. Prov. App. No. 62/396,197 filed on Sep. 18, 2016, which is hereby incorporated by reference in its entirety.

BACKGROUND

Field of the Invention

Certain embodiments of the invention relate to medical applications, including orthopedic surgery, but also in any area of surgery (including veterinary medicine) where a wire needs to be passed around a bone (or other body structure), such as fracture care or in the treatment of major joint reconstruction, especially revisions.

Description of the Related Art

A cerclage device is used by orthopedic surgeons and other practitioners of the healing arts to allow a bone to be encircled and held together with a wire or cable. Such devices can secure bone fracture fragments, and/or reinforce a long bone from hoop stress. Secure fixation requires prevention of interposition of soft tissue between the cable/wire and bone. Soft tissue prevents adequate tightening of the wire or cable. In addition, interposition of soft tissue poses a safety risk as that soft tissue may include vital structures such as nerves or blood vessels. These devices can find application in several areas of surgery. For example, in the treatment of fractures of long bones, it is frequently necessary to supplement intramedullary or bone plate fixation. Periprosthetic fractures subjected to plate fixation require cerclage fixation because screw fixation can impinge on the prosthesis. Furthermore, structural bone-grafts for non-unions or after revision joint reconstruction can require secure fixation in order to heal to native bone. Finally, cerclage is often used to negate hoop stresses in primary hip, knee, and shoulder replacement when the prosthesis insertion has resulted in a longitudinal crack in the bone, such as the femur. In some cases, conventional cerclage passers can be associated with morbidity/complications such as vascular or nerve injury caused because the cerclage or wire is passed too far away from the surface of the bone, and blood vessels, nerves, and other structures can be impinged by the cerclage or wire. Devices and methods that can better enable safe and efficient placement of cerclage wires or cables in any situation, and in some cases as close to the bone as possible are needed.

SUMMARY

In some embodiments, disclosed herein is a cerclage wire or cable passer that can include any number of features disclosed herein. The passer can include any number of the following, including: a flexible tube that includes a first surface and a second surface opposite the first surface. The first surface can be substantially flat and configured to contact an outer surface of the bone and lie flat on the bone as it is passed around the bone. The flexible tube can further include a proximal end, a distal end, a lumen configured to house a wire or cable therethrough, and an elongate body therebetween. The distal end can include a curved shape. The passer can also include an appendage guide that includes an open proximal end and an open or closed distal end. The appendage guide can be directly adjacent the second surface of the flexible tube. The appendage guide can be configured to house the distal phalanx of a finger of an operator. The distal end of the appendage guide can define the transition from the elongate body of the flexible tube to the curved distal end of the flexible tube extending distally past the distal end of the appendage guide. In some embodiments, the passer can be configured to be sufficiently flexible to conform to the radius of curvature of the bone from pressure from the finger. In some embodiments, the appendage guide comprises a smooth surface radially inward and/or outward surface. In some embodiments, the appendage guide is configured to allow passage of the guide through tissue, and sized to hold the distal phalanx of the finger securely and allow tactile appreciation for a location of the curved distal end of the flexible tube. In some embodiments, the distal end of the flexible tube comprises a constant, or variable radius of curvature. The flexible tube can have a length sufficient that the finger in the appendage guide does not completely encircle the bone, to allow retrograde passage of the wire/cable. The bone could be, in some cases, a tibia, fibula, humerus, femur, or other desired bone. The cerclage passer can include a hinge. The appendage guide can include a slot and/or an area of reduced thickness to increase flexibility of the appendage guide.

The flexible tube can also be of sufficient rigidity that the guiding finger can discern the position of the curved distal end of the flexible tube against the bone by friction, preventing soft tissue interposition between the cerclage passer and the bone. The appendage guide can include a clip in some cases. The flexible tube can include a variety of cross-sections, including a rectangular, square, semi-circular (including but not limited to semi-oval), or other cross-sections. The flexible tube can include a slot to increase flexibility of the flexible tube.

In some embodiments, disclosed herein is a cerclage passing system configured to pass multiple wires or cables around a bone or other body structure, such as simultaneously. The system can include, for example, a first cerclage passer, a second cerclage passer, and in some cases a third, fourth, and/or fifth cerclage passer. The first cerclage passer and the second cerclage passer can be configured to be attached via a connector positioned proximal to the appendage guides of the first cerclage passer, second cerclage passer, and additional cerclage passers if present. Any number of cerclage passers can be permanently or removably attached or attachable via one, two, or more connectors.

Also disclosed herein are methods of passing a tether around a bone or other body structure. The methods can include, for example, any number of the following: providing a first cerclage passer, providing a second cerclage passer, connecting the first cerclage passer to the second cerclage passer in parallel, placing a first finger into the appendage guide of the first cerclage passer, placing a second finger into the appendage guide of the second cerclage passer, passing the first cerclage passer and the second cerclage passer directly adjacent to and circumferentially around an outer surface of the bone, passing a first tether through the lumen of the first cerclage passer, passing a second tether through the lumen of the second cerclage passer; and withdrawing the first and second cerclage passers, thereby placing the first tether and the second tether at a desired distance from each other and around the bone. The methods can also include providing a third cerclage passer, and connecting the third cerclage passer to the first cerclage passer and the second cerclage passer in parallel.

Also disclosed herein are methods of passing a tether, such as a wire or cable for example, around a bone or other body structure. The method can include, for example, providing a cerclage passer, providing a tether comprising a proximal end, a distal end, an elongate body, and a locking mechanism attached proximate the distal end of the tether; inserting the proximal end of the tether into the lumen at the distal end of the cerclage passer; passing the tether in a retrograde direction and around a bone without removing the locking mechanism from the tether; locking the distal end of the tether to another portion of the tether to form a loop around the bone; and withdrawing the cerclage passer, leaving the tether loop in place around the bone.

DETAILED DESCRIPTION

Figure 1:
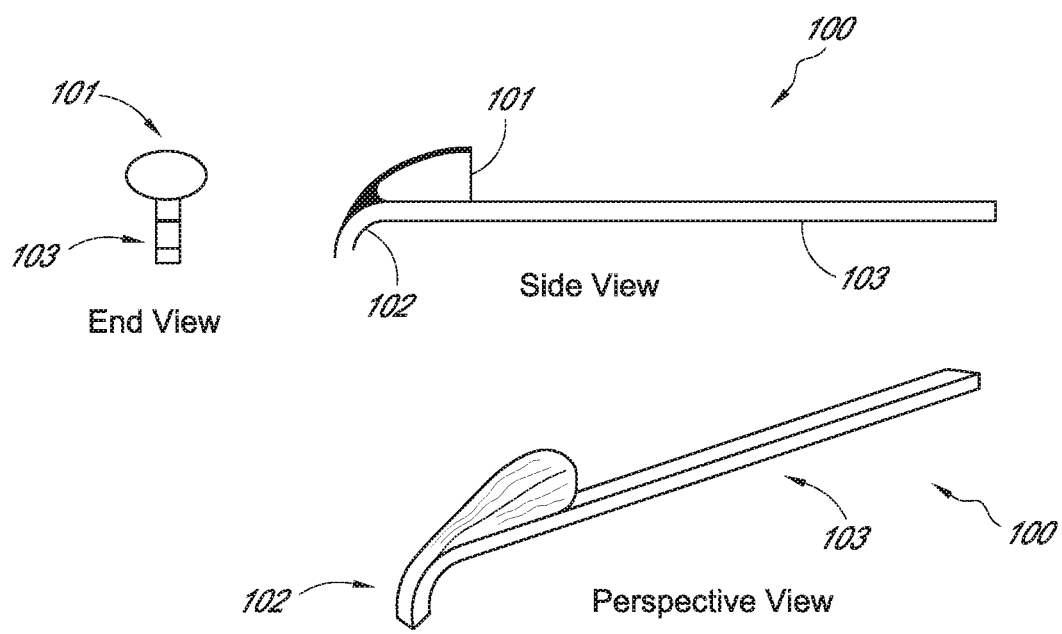
FIG. 1 illustrates an end view, side view, and perspective view of a cerclage passer device, according to some embodiments of the invention.

Cerclage devices for passing a wire or cable around a bone have been in surgical practice for many years. Many of these devices are rigid "C" or "S" shaped tubes with a handle. These can be clumsy and difficult to use because of their rigidity. In order to accommodate large and small bones, they have a much larger radius of curvature than the bone and they are, therefore, difficult to keep the tip close to the bone to avoid soft tissue interposition. If the cerclage passer has a small arc, it can tend to trap soft tissue because it may not be able to reach all the way around the bone. If the cerclage passer has a large arc, it may have to be turned sideways, parallel to the length of the bone to get started around the bone, requiring a more extensive dissection.

Other forms of passers incorporate minimally invasive devices which can depend on a coil of wire, tube, or a spring plate to conform to the shape of the bone as it is passed into the wound. These devices may have no way to tell if they have really prevented the soft tissue from being trapped. Further potential problems with these conventional devices include difficulty cleaning them for re-use, difficulty assembling for passing the wire, and excessive trauma to the tissues from multiple attempts to pass the wire/cable. These devices often claim minimally invasive technique, but the more minimally invasive the technique, the more likely the possibility of tissue interposition. These devices can lack the true tactile sensation provided by a surgeon's finger which is able to feel the bone surface during passage of a device, due to the curved end of the tube as disclosed in certain embodiments of the invention herein, which can be advantageously akin to a long fingernail.

Systems and methods are disclosed which can provide a safe means of passing a cerclage wire around a bone. Embodiments of techniques for accomplishing this task are also described. Some embodiments use the tactile sensation of the human hand to achieve appropriate placement of the cerclage wire. Thus, irregularities in the bone fragments of a fracture or bone graft augmenting a fracture can safely be encircled and secured. The device can advantageously permit retrograde placement of the cerclage wire compatible with available manufactured devices.

In some embodiments, devices and methods for passing a retrograde cerclage wire around a bone are disclosed. The devices can include an appendage guide (that can be similar to a thimble in some cases) to house a distal portion of an operator's finger attached to a tube that is guided around a bone or other anatomical structure of interest to allow placement of a cable, wire, or tether safely encircling the bone. In some embodiments, a cerclage device includes a flat or substantially flat tube which can allow the tube to lie flat on the surface of the bone. In some embodiments, the tube may be of any shape in external or internal cross-section as long as the surface against the bone is flat or substantially flat. The cerclage wire passer device can be attached to an appendage guide, which can be in some cases a thimble-like device to enclose a fingertip. The appendage guide can be, in some cases, partially or entirely radially offset from the tube. The tube can be in some cases rigid or flexible and extend a distance (distally) past the tip of the finger on the order of, for example, between about 1 cm to about 3 cm, and can be flexible or rigid and curved in this region, such that it conforms to the curvature of the bone. In some embodiments, a proximal linear segment of the tube can have the same flexibility, increased flexibility, or decreased flexibility with respect to the curved distal end of the tube. In some embodiments, the tube and the appendage guide can be made of different materials or the same material.

The tube can extend proximally from the distal end of the fingertip or appendage guide a desired distance, which can be, for example, approximately 10-30 cm, 15-20 cm, or about 5 cm, 10 cm, 15 cm, 20 cm, 25 cm, 30 cm, 35 cm, 40 cm, or ranges incorporating any two of the aforementioned values in some cases. The appendage guide element of the device can be placed on a finger, placed directly against the exposed bone without or substantially without any intervening soft tissue, nerves, or muscles, and passed around the bone, close to the surface of the bone under direct pressure until it has come all the way around the bone so that the tip of the device is visible on the opposite side of the bone. In some embodiments, the appendage guide element is placed no more than about 10 mm, 9 mm, 8 mm, 7 mm, 6 mm, 5 mm, 4 mm, 3 mm, 2 mm, 1.5 mm, or 1 mm or 0.5 mm or less radially outward from the surface (e.g., outer cortical surface) of the target bone, or directly in contact with/on the surface of the target bone. In some embodiments, the devices and methods as disclosed herein can advantageously prevent interposition of soft tissue due to the use of tactile sensation provided by the finger and the curved tip of the device. This sensation allows guiding the device closely to, or in direct contact with the surface of the bone. It is then possible to pass the wire or cable retrograde into the distal end of the lumen at the distal tip (e.g., the curved distal end) of the device which is distal to the fingertip and out the lumen at the proximal end of the flexible tube of the device. Alternatively, the wire or cable can be placed in an antegrade manner into the lumen at the proximal end of the flexible tube if, for example, the wire/cable has no integral locking device. Some conventional cables include an attached locking mechanism, such as on or near a proximal or distal end of a cable. The locking mechanism can permit adjustment and secondary re-tightening of the cable, which can be advantageous in some cases as the addition of more cable takes stress off the first cables, requiring them to be retightened. These locking devices are typically too large to fit through conventional cable passers. The finger and the device can be withdrawn around the bone bringing the cable/wire with it, if placed retrograde. When the wire/cable is placed antegrade, the wire protruding from the device can be grasped to prevent it moving while the device is withdrawn. Various cables with locking mechanisms are commercially available and may be used. The wire/cable is then secured to the bone after tightening with the locking mechanism. In one embodiment, the appendage guide is flexible and elastic so that the appendage guide conforms to the shape of the finger to make a lower profile for withdrawing the device and to make it so that it fits any finger.

FIG. 1 includes side, end, and perspective views of one embodiment of a cerclage passer device 100. The cerclage passer device 100 can include a somewhat flexible appendage guide 101 which in some embodiments can resemble a thimble and configured to reversibly hold a fingertip. The appendage guide 101 can, for example, include an open proximal end, a tubular sidewall, and a closed distal end and configured to hold a finger, such as an index finger for example. In other embodiments, the appendage guide 101 can have an open distal end, taking the form of a ring-like structure. The appendage guide 101 can have a constant outer and/or inner diameter from the proximal end to the distal end, or have a diameter that tapers and becomes smaller at the distal end relative to the proximal end. In some embodiments, the cerclage passer device 100 includes a curved distal end 102 to help the cerclage passer 100 conform to the shape of the bone. The curved distal end 102 can be relatively rigid in some embodiments with respect to a proximal portion or end of the cerclage passer 100, and the curve can extend inferiorly as illustrated, or superiorly in other embodiments. In some embodiments, the curve can have an arc with a subtended angle, for example, of between about 30 degrees and about 150 degrees, or between about 60 degrees and about 120 degrees, or about 90 degrees with respect to the longitudinal axis of a segment of the tube 103. The radius of the curve can vary, for example, between 10 mm and 20 mm, between about 10 mm and about 40 mm, or between about 5 mm and about 30 mm, or about 5 mm, 10 mm, 15 mm, 20 mm, 25 mm, 30 mm, 35 mm, 40 mm, 45 mm, or ranges including any two of the foregoing values. In some embodiments, the radius of curvature can be about or more than about 30 mm, 35 mm, 40 mm, or more because to get around the bone, the arc may need to be on the order of, e.g., about 200-330 degrees, or about 240-300 degrees, such as about 270 degrees, and the space between the tip and the remainder of the device can be preferably larger than the target bone diameter, which is for the femur in some cases from about 35 mm to about 50 mm Also illustrated is the flexible tube 103, which can have a flattened cross-section, such as square or rectangular for example. In some embodiments, the tube 103 can have any cross-sectional shape, but preferably has a flat surface that comes into contact or close proximity to a bony surface. The tube 103 can include one, two, or more lumens therethrough configured to pass a wire, cable, suture, or other elongated member therethrough. The appendage guide 101 can be positioned in some embodiments entirely spaced radially apart from the flexible tube 103, and/or opposite the surface of the flexible tube 103 that comes into contact with the bone, which can be a relatively flat surface in some cases. In some embodiments, the distal end of the appendage guide 101 is coincident with the proximal end of the curved distal end 102 of the cerclage passer device 100. In one embodiment, the appendage guide 101 can include, or take the form of a clip to reversibly hold the proximal phalanx. The entire device or portions thereof can be constructed, for example, of a flexible, sterilizable, polymeric material that can be discarded after one-time use. Alternatively, a metallic or other version could be constructed for multiple uses.

Figure 2:
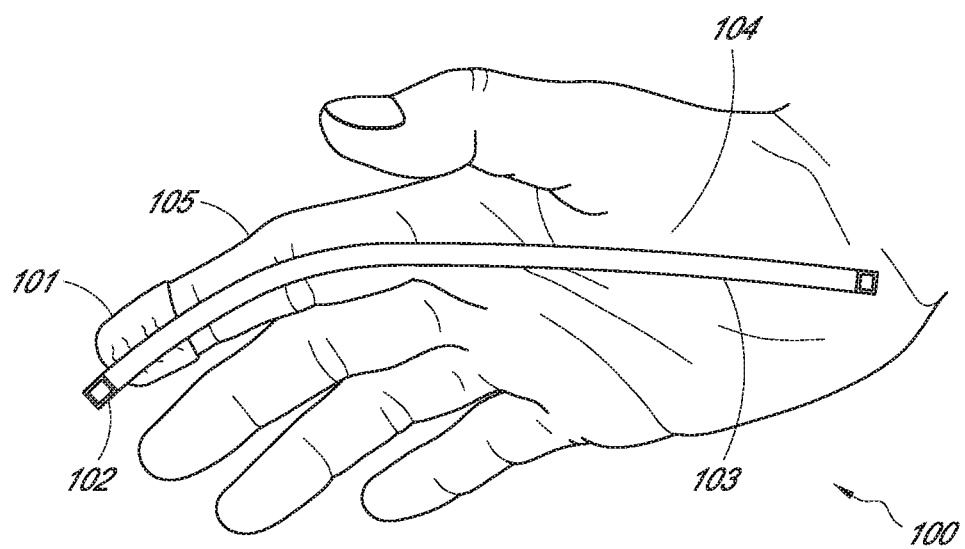
FIG. 2 illustrates an embodiment of a cerclage passer device, with an appendage guide element in place on the volar surface of the index finger.

FIG. 2 illustrates an embodiment of the device 100 in place on the right index finger 105. The curved distal end 102 can extend axially distally beyond the distal end of the appendage guide 101 and the finger therein. The tube 103 can lie along the palm of a hand 104 and extend proximally as shown.

Figure 3:
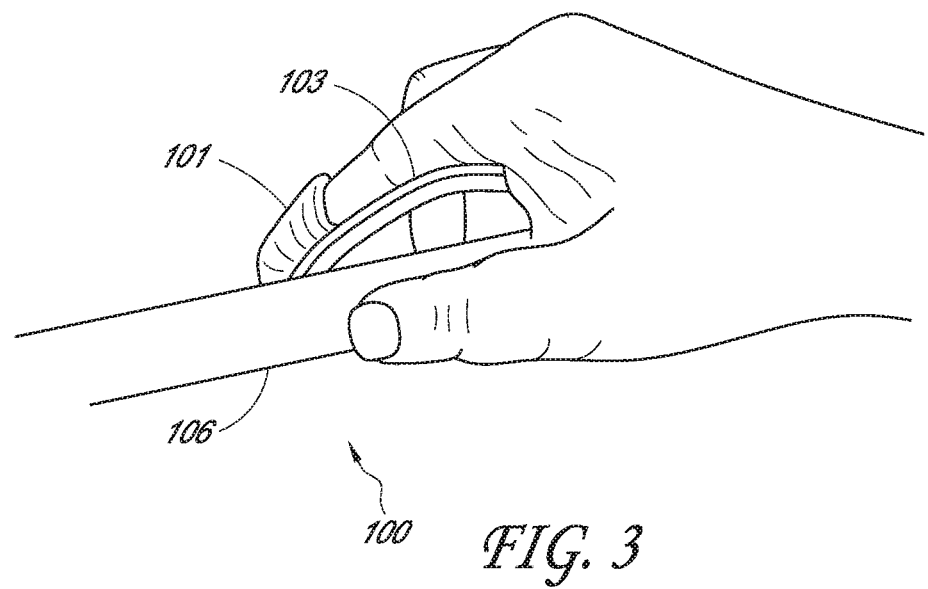
FIG. 3 shows an embodiment of a cerclage passer device being slid over the top of a bone in close contact to the bone as palpated by the finger, according to some embodiments of the invention.

FIG. 3 illustrates an embodiment of the device 100 passing along the surface of the bone 106 where wire/cable placement is desired. With the curved distal end 102 as a "feeler", the device 100 is able to maintain continuous or substantially continuous contact with the outer surface of the bone 106, to prevent undesirable interposition of soft tissue, nerves, blood vessels, and the like, as the index or other finger guides the curved distal end 102 around the bone. In one embodiment, the radius of curvature on the curved point is not constant, but is variable (greater or lesser) to ensure that the curved distal end 102 can stay in contact with the bone 106 including both large diameter and small diameter bones.

Figure 4:
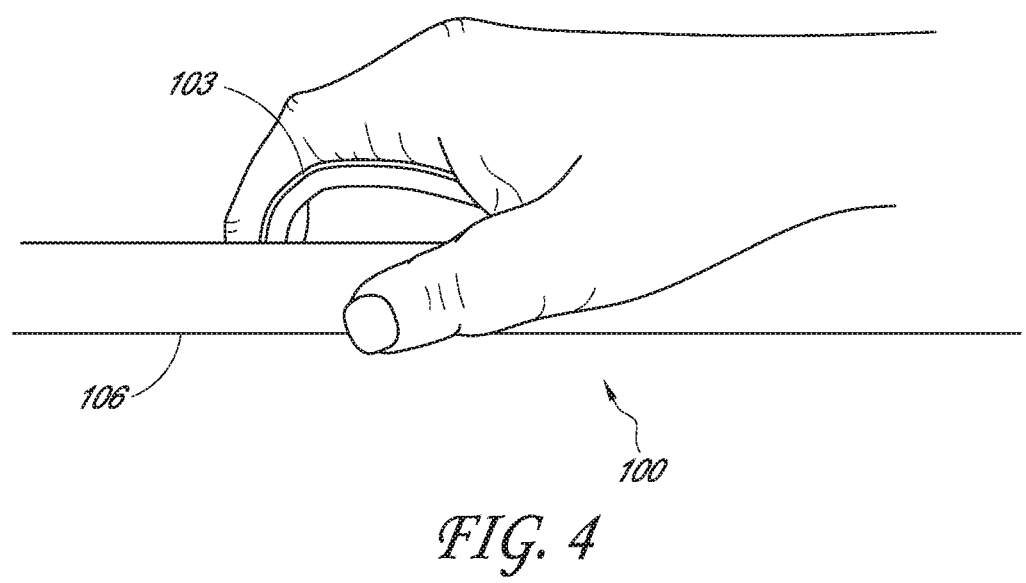
FIG. 4 shows the progression of a cerclage passer device around the bone with the leading edge of the extension tube in contact to the bone, according to some embodiments of the invention.

FIG. 4 shows the device 100 nearly entirely circumscribing the bone 106. The tube 103 is in contact with the bone 106 beneath the finger 105, ensuring or reducing the likelihood that the wire/cable will not trap any soft tissue.

Figure 5:
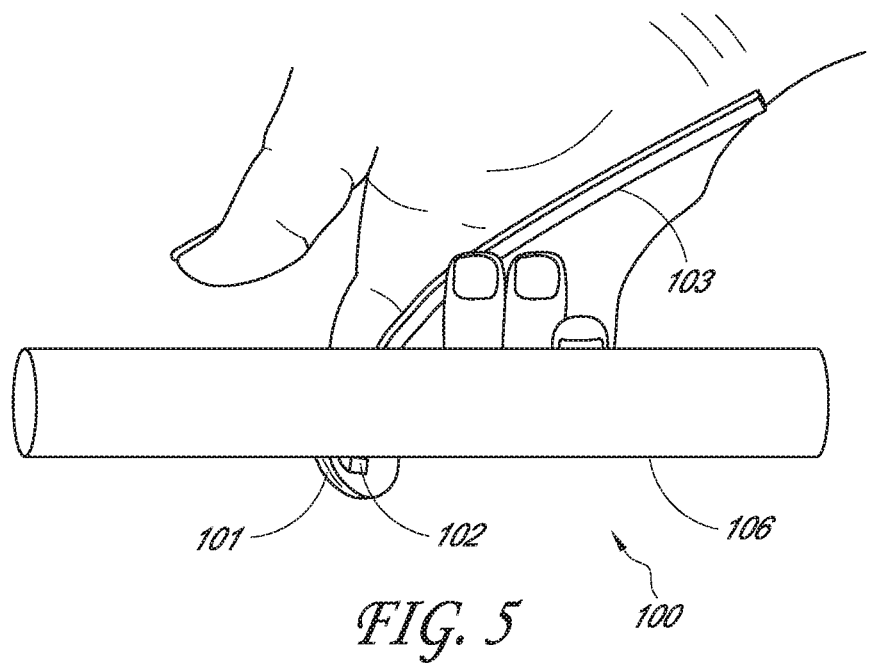
FIG. 5 shows an embodiment with the cerclage passer device appearing on the other surface of the bone, according to some embodiments of the invention.

FIG. 5 shows the tip of the curved distal end 102 rounding the bone 106. The tube 103 portion of the device is in the palm 104 of the hand except where it is in direct contact with the bone 106.

Figure 6:
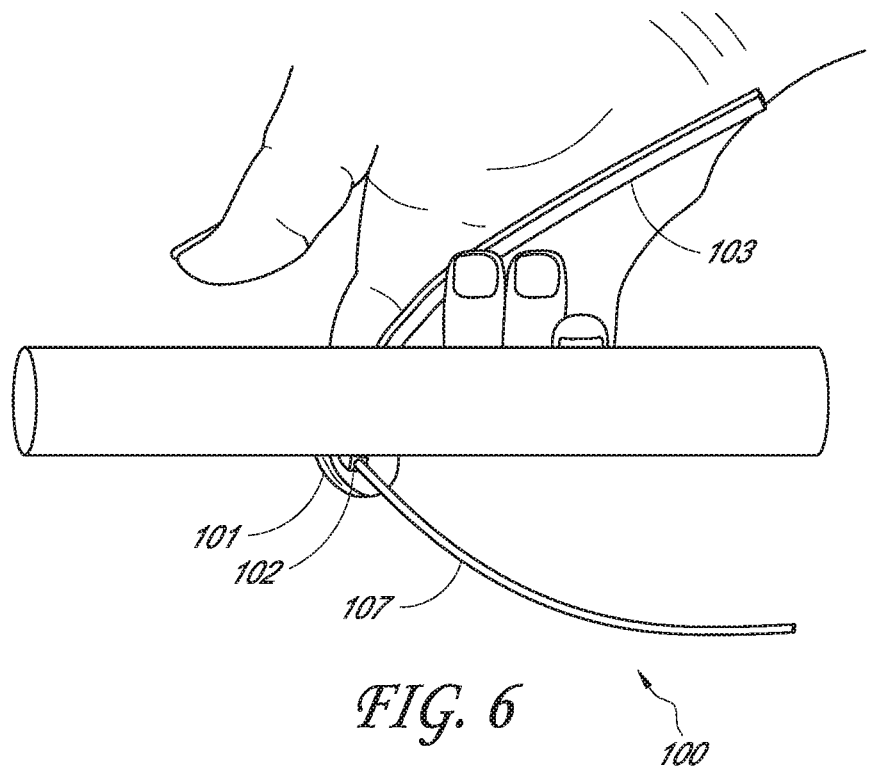
FIG. 6 shows the wire placed into a lumen of the tube of the device, completing the encircling of the bone, according to some embodiments of the invention.

FIG. 6 shows a wire/cable 107 inserted into the end of the curved distal end 102 of the wire/cable passer device 100. The device 100 is then withdrawn from the wound and the wire/cable is then secured to the bone with no intervening soft tissue.

Figure 7:
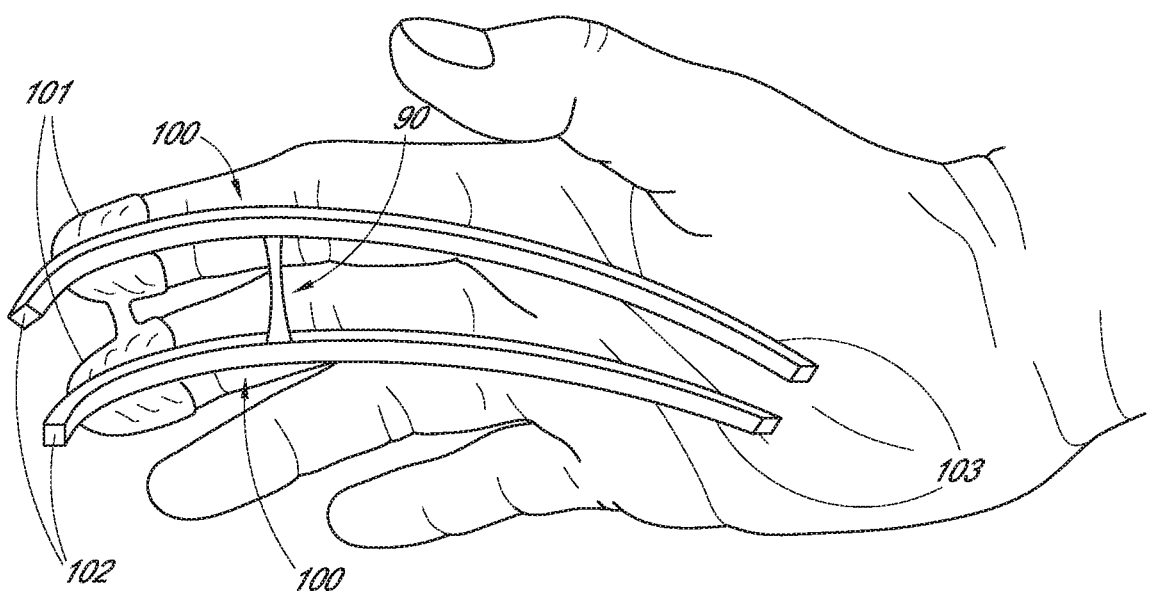
FIG. 7 illustrates a cerclage passing system including a plurality of cerclage passers connected in parallel for passing multiple wires or cables at the same time, according to some embodiments of the invention.

In another embodiment, two, three, or even more of the devices may be attached to each other (e.g., such as in parallel to each other) to allow 2, 3 or 4 wires to be passed simultaneously. One such embodiment is shown in FIG. 7, illustrating a plurality of devices 100 attached side-by-side via a connector 90. The connector 90 can be placed at any appropriate location between connected devices, such as, for example, proximal to the segments of the devices attached to appendage guides 101 and curved distal ends 102 as shown. In some embodiments, the connector 90 forms an H-shape as shown with the devices 100. In some embodiments, the longitudinal axis of the connector 90 can be transverse to the longitudinal axis of the passing devices 100 as shown, or at oblique or other angles. The connectors 90 can include attachable or detachable elements such as clips, complementary interference fits, threaded elements, etc. in some embodiments to allow for modular addition of devices together as well as subtraction depending on the number of wires desired and the desired clinical result. In other embodiments, the plurality of devices 100 can be pre-connected or permanently connected together. A device including three passing devices 100 can include two connectors 90 side-by-side in some embodiments. The second, third, or fourth wire/cable passer could be placed on, for example, the long, ring, or little fingers. All the fingers could be passed around the long bone simultaneously and the wires/cables inserted into the device. In some embodiments, the spacing between fingers provides nearly optimal spacing for sequential wires.

Figure 8:
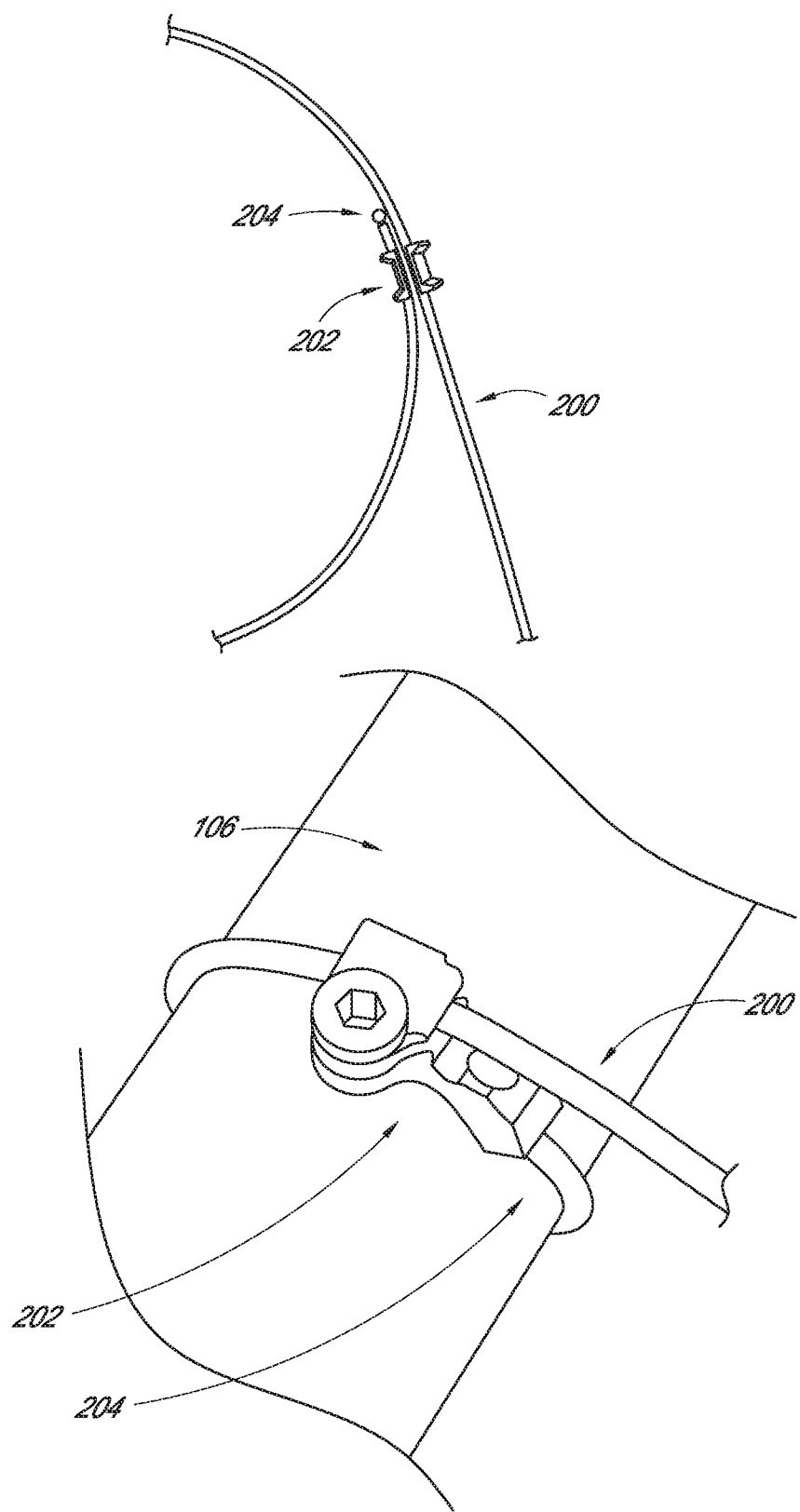
FIG. 8 illustrates various wires or cables including locking mechanisms.

As noted above, in some embodiments, a wire or cable having a locking mechanism attached thereto can be passed in an anterograde (e.g., proximal to distal) or retrograde (e.g., distal to proximal) manner. For example, a wire or cable can have a locking mechanism attached proximate or near a first or second end (e.g., a distal end of the wire of cable. FIG. 8 illustrates embodiments of cables 200 including locking mechanisms 202 at or near the distal end 204 of the wire or cable that are too bulky to pass through a lumen of wire or cerclage passers. The end of the wire or cable without the locking mechanism attached (e.g., a proximal end) can be inserted into a lumen of the curved distal end 102 of the passing device 100 (not shown in FIG. 8) and then threaded proximally until the wire or cable exits the lumen at the proximal end of the passing device 100. The wire or cable 200 can thus be advantageously passed in a retrograde manner while the locking mechanism 202 remains attached to the wire or cable. While in some embodiments an operator can remove the locking device, pass the wire or cable antegrade, and then attach or reattach the locking mechanism, the retrograde method can be simpler and save significant time in some cases.

Figure 9:
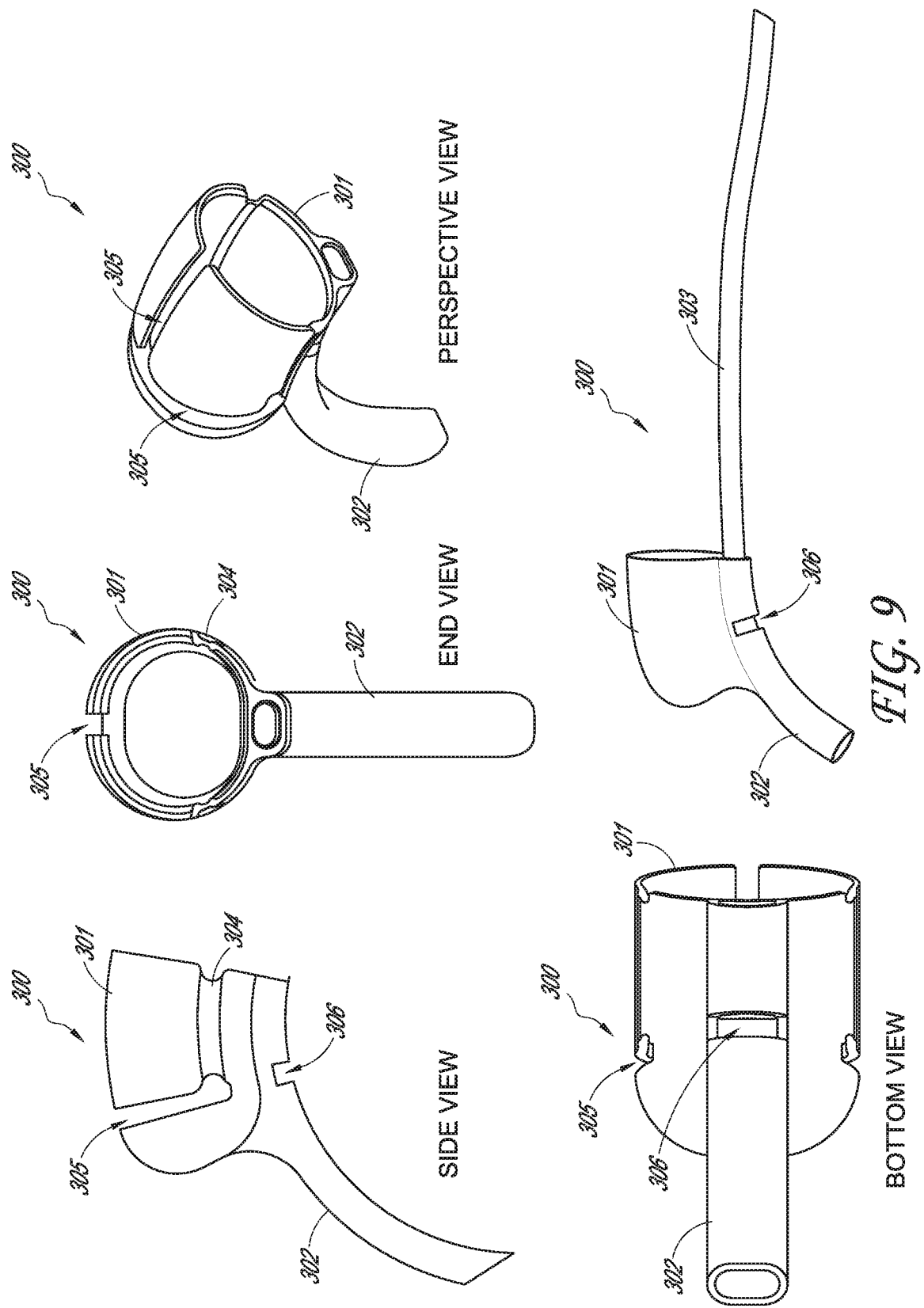
FIG. 9 illustrates an embodiment of a cerclage passer device with features to accommodate various finger sizes.

FIG. 9 includes side, end, perspective, and bottom views of a cerclage passer device 300. The cerclage passer device 300 can include an appendage guide 301 configured to reversibly hold a fingertip. The appendage guide 301 can include an open proximal end, a tubular sidewall, and a distal end. The curved distal end 302 can extend axially and distally beyond the distal end of the appendage guide 301. The curved distal end 302 connects to a tubular structure 303. The tubular structure 303 can extend axially along the appendage guide 301 and proximally from the appendage guide 301.

The cerclage passer device 300 can include a connection between the tubular structure 303 and the appendage guide 301. The connection can be an area of reduced thickness or a slot. The cerclage passer device 300 can include at least one region of reduced wall thickness to increase flexibility. The cerclage passer device 300 can include at least slot to increase flexibility. The connection can allow the appendage guide 301 to flex relative to the tubular structure 303. The connection can be a hinge, such as a living hinge in some cases.

The cerclage passer device 300 can include one or more regions of reduced wall thickness 304. The region can decrease the thickness of the tubular sidewall of the appendage guide 301. The cerclage passer device 300 can include two regions to enable each side of the appendage guide 301 to flex. In some embodiments, the cerclage passer device 300 does not include the regions of reduced wall thickness 304.

The cerclage passer device 300 can include a slot 305. The slot 305 can include a first segment located opposite to the tubular structure 303, along a midline of the appendage guide 301. The slot 305 can include a second segment located circumferentially around the appendage guide 301, or a portion thereof. The second segment can extend for a portion of the circumference (e.g., about, at least about, or no more than about 30%, 40%, 50%, 60%, 70%, 80%, or more or less, etc.). The slot 305 can have a T-shaped configuration with the first segment and the second segment. The appendage guide 301 therefore can comprise two panels with added flexibility due in part to the slot 305. Each panel can include a region of reduced wall thickness 304. The regions of reduced wall thickness 304 can intersect with the second segment of the slot 305. The region of reduced wall thickness 304 can facilitate the widening of the slot 305 by allowing the panels of the appendage guide 301 to flex outward. In some embodiments, the cerclage passer device 300 does not include the slot 305.

The cerclage passer device 300 can include a bottom slot 306. The bottom slot 306 can be aligned with the second segment of the slot 305. The bottom slot 306 can be located circumferentially around the cerclage passer device 300, or a portion thereof. The bottom slot 306 can extend for a portion of the circumference (e.g., about, at least about, or no more than about 5%, 10%, 15%, 20%, 25%, etc.). The bottom slot 306 can interrupt the curved distal end 302. The curved distal end 302 therefore comprises added flexibility due in part to the bottom slot 306. In some embodiments, the cerclage passer device 300 does not include the bottom slot 306.

The cerclage passer device 300 can allow various size fingers to be accommodated by changing the finger structure of the device. The appendage guide 301 can have the ability to flex to accommodate larger fingers. The connection including regions of reduced thickness and/or slots can form a movable structure such as a hinge to allow the appendage guide 301 to flex. The user can exert more force on the tip of the appendage guide 301 to force the curved distal end 302 to conform to the bone. The regions of reduced thickness 304 and/or the slots 305, 306 may allow the user to rotate the finger to apply a different force vector on the curved distal end 302. This change in the trajectory of force may allow the distal end 302 to conform more closely to the curvature of the bone.

Other configurations are contemplated. In the fully attached appendage guide described herein, the appendage guide may be partially detached proximally to allow more flexibility of the curved distal end. This would effectively reduce the radius of curvature of the appendage guide allowing it to conform more readily to the bone.

Figure 10:
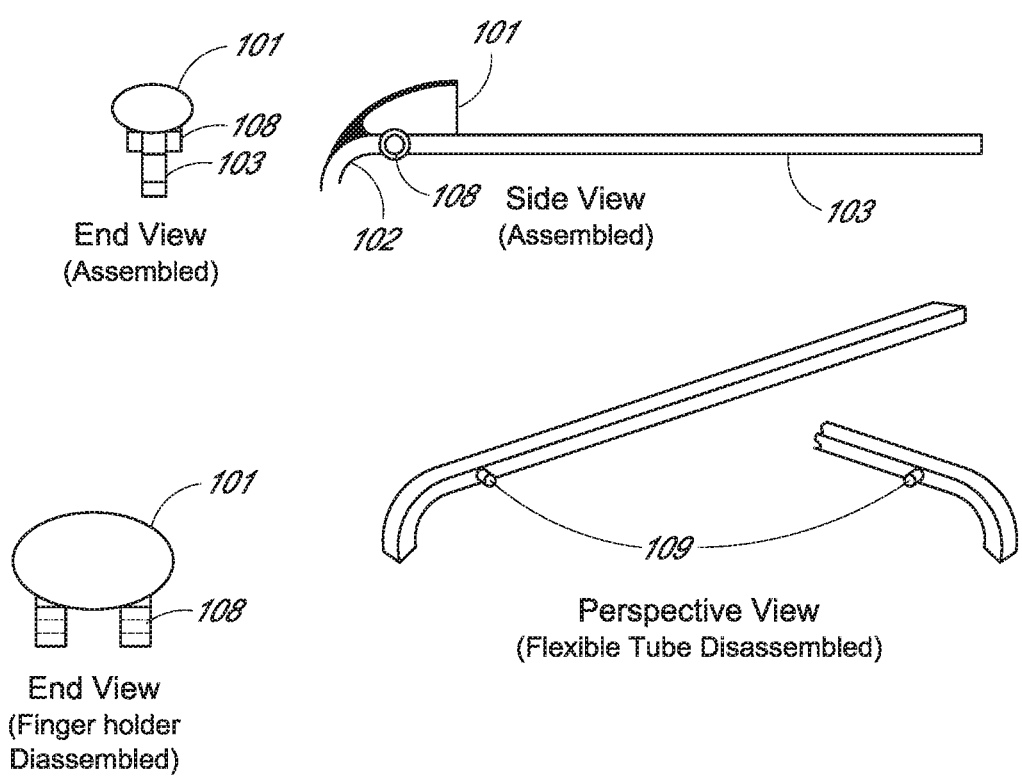
FIG. 10 illustrates an embodiment of a cerclage passer device with a hinge.

FIG. 10 includes side, end view of the assembled device, end view of embodiments of the disassembled device, and a perspective view of a modification to the cerclage passer device 100 described herein according to some embodiments of the invention. The cerclage passer device 100 can include the appendage guide 101 into which a fingertip is configured to be inserted. The appendage guide 101 can include an open proximal end for finger insertion, a tubular sidewall to surround the finger, and a closed distal end near the fingertip. The appendage guide 101 can have a decreasing outer and/or inner diameter from the proximal end to the distal end. In some embodiments, the cerclage passer device 100 includes the curved distal end 102 which curves around the bone. In some embodiments, the cerclage passer device 100 includes the tube 103. The tube 103 can have any cross-section, such as round, square, or rectangular. The tube 103 can include a lumen configured to pass a wire, cable, suture, or other elongated member therethrough. In some embodiments, the curved distal end 102 and the tube 103 are integrally or monolithically formed as a single component. In some embodiments, the curved distal end 102 and the tube 103 are rigid or substantially rigid.

FIG. 10 includes a mechanism 108 for allowing the finger to apply more pressure to the tip of the curved distal end 102 to keep the curved distal end 102 closely applied to the bone. The mechanism 108 can be a hinge. The mechanism 108 can be placed at any location relative to the appendage guide 101. In the illustrated embodiment, the mechanism 108 is placed about midway along the bottom of the appendage guide 101. In some embodiments, the mechanism 108 can attach to the tube 103 along the length thereof In some embodiments, the mechanism 108 can attach to the curved distal end 102 along the length thereof. The mechanism 108 can include one or more solid cylindrical extensions 109. In the illustrated embodiment, the mechanism 108 can include two solid cylindrical extensions 109 extending perpendicularly from the tube 103, parallel to the bone. The two solid cylindrical extensions 109 can be coaxial. The two cylindrical extensions 109 can allow the appendage guide 101 to equally pivot about a center of rotation. Other configurations are contemplated.

The mechanism 108 can allow the distal end of the cerclage passer device 100 to apply force to the distal end of the curved distal end 102, such that the force of the finger is now applied at the end of the appendage guide 101. The mechanism 108 can allow the appendage guide 101 to pivot relative to the cylindrical extensions 109. The mechanism 108 can allow the appendage guide 101 to pivot such that the vector of the force applied by the finger changes directions, such as with respect to the longitudinal axis of the proximal portion of the device 100 such that the proximal open end of the appendage guide 101 is not parallel, or at a tangent to the longitudinal axis of the proximal portion of the device 100. The mechanism 108 can allow the appendage guide 101 to pivot to align the force of the finger with the curved distal end 102. The mechanism 108 can serve other purposes in that the mechanism 108 can allow the cerclage passer device 100 to be changed or switched out to accommodate larger or smaller fingers. For example, the mechanism 108 can allow a larger appendage guide 101 to be affixed to the curved distal end 102 and the flexible tube 103 to accommodate a larger finger. The cerclage passer device 100 can be changed to accommodate larger or smaller fingers in other ways. In some embodiments, two or more components are separable and changeable for differently sized components. The proximal part of the appendage guide 101 can be separated from the tube 103. The proximal part of the appendage guide 101 can be separated from the curved distal end 102.

The mechanism 108 can be positioned between the appendage guide 101 and another component of the cerclage passer device 100. The mechanism 108 provides for pivoting articulation for the appendage guide 101. In some embodiments, the mechanism 108 comprises a single hinge. In some embodiments, the mechanism 108 comprises a pair of hinges. Other mechanical mechanisms that allow for articulation of the appendage guide 101 are contemplated.

In some embodiments, the finger of the user is completely enclosed. In some embodiments, the fingertip of the user does not extend outward from the appendage guide. In some embodiments, the finger of the user does not extend distally from the appendage guide. In some embodiments, the finger of the user extends only proximally from the appendage guide. An advantage is that the user can direct a force onto the curved distal end. An advantage is that the finger is protected. In some embodiments, the finger of the user is partially enclosed. In some embodiments, the finger of the user is partially enclosed but the distal tip of the finger is fully enclosed. Some advantages of certain embodiments include one or more of the following: the appendage guide can flex to accommodate larger fingers; the appendage guide can flex to direct the force applied by the finger; and/or the appendage guide can be directed as an extension of the finger. In some embodiments, the appendage guide tapers from the proximal end to a distal end of the appendage guide. Another advantage, in some cases, is that the appendage guide can direct the force from the finger to the distal end of the appendage guide.

In some embodiments, the appendage guide and/or the curved distal end can provide tactile feedback related to the anatomy of the patient. The appendage guide and/or the curved distal end can be able to pass through tissue but not bone. The appendage guide and/or the curved distal end can be able to pass through muscle but not bone. In some embodiments, the fingertip of the user applies the force (e.g., through a poking action). In some embodiments, the force vector is along the longitudinal axis of the finger. In some embodiments, the finger pad of the user does not applies the force (e.g., through a pressing action). In some embodiments, the force vector is not perpendicular to the longitudinal axis of the finger.

In some embodiments, the appendage guide accommodates the finger tip of the user. In some embodiments, the appendage guide accommodates the first joint of the finger of the user. In some embodiments, the appendage guide accommodates the first joint and the knuckle of the finger of the user. In some embodiments, the appendage guide encloses the distal phalanx. In some embodiments, the appendage guide encloses the distal phalanx and at least a portion of the middle phalanx. In some embodiments, the appendage guide encloses the distal phalanx and the middle phalanx. In some embodiments, the appendage guide encloses the distal phalanx, the middle phalanx and at least a portion of the proximal phalanx.

In some embodiments, the appendage guide can accommodate different sized fingers. In some embodiments, the appendage guide can include a hinge. In some embodiments, the appendage guide can include an area of reduced wall thickness. In some embodiments, the appendage guide can include one or more slots. An advantage is that appendage guide can include a low-profile hinge. An advantage is that appendage guide can allow for different positions of the finger relative to the distal end of the appendage guide. An advantage is that appendage guide can be configured to flex around the finger of the patient. An advantage is that appendage guide can fit snugly against the finger. An advantage is that appendage guide can grip and hold the finger. In some embodiments, the hinge is formed in the wall of the appendage guide. An advantage is that the hinge incorporates no additional components. An advantage is that the hinge is easy to manufacture. An advantage is that the hinge reduces inventory by reducing the number of appendage guides needed to fit the majority of fingers of orthopedic surgeons. An advantage is that the hinge allows the user to flex his or her finger.

In some embodiments, the hinge is formed in the wall of the curved distal end. An advantage is that the hinge allows the user to keep the curved distal end on the bone. In some embodiments, the hinge is formed between the curved distal end and the flexible tube. In some embodiments, the user can feel the bone as the curved distal end is passed around the bone. An advantage is that the user can more easily direct the curved distal end around the bone. In some embodiments, the user can be much closer to the application of force. An advantage is that the user can more accurately direct the force. An advantage is that the user can use less force. An advantage is that that user can avoid or reduce injuries from erroneous applications of force.

In some embodiments, the appendage guide can be substituted for another appendage guide. An advantage is that a system can include two or more appendage guides. An advantage is that a system can include two or more appendage guides of different sizes. An advantage is that a system can include two or more appendage guides of different configurations. An advantage is that a system can allow for interchangeable another appendage guide. In some embodiments, the appendage guide can have a low profile. In some embodiments, the appendage guide can be thin. In some embodiments, the appendage guide can be disposable. In some embodiments, the flexible tube can be substituted for another flexible tube. An advantage is that a system can include two or more configurations of flexible tubes. In some embodiments, the integrally formed curved distal end and tube can be substituted for another curved distal end and tube.

In some embodiments, the appendage guide and the curved distal end are integrally or monolithically formed. In some embodiments, the appendage guide and the curved distal end are separate components. In some embodiments, the appendage guide and the flexible tube are integrally or monolithically formed. In some embodiments, the appendage guide and the flexible tube are separate components.

In some embodiments, the distal end of the device is curved. An advantage is that the curved distal end extends beyond the appendage guide. An advantage is that the curved distal end matches the curvature of a bone. An advantage is that the curved distal end follows the shape of the bone. In some embodiments, the curved distal end forms a portion of a circumference of a circle (e.g., about 20%, 30%, 40%, 50%, 60%, 70%, 80%, or ranges incorporating any two of the aforementioned values, etc.). An advantage is that the curved distal end encircles a portion of the bone. An advantage is that the user's finger does not need to circumvent the entire bone. In some embodiments, the user circumvents only a portion of the bone (e.g., about 20%, 30%, 40%, 50%, 60%, 70%, 80%, or ranges incorporating any two of the aforementioned values, etc.). In some embodiments, the curved distal end is narrower than the appendage guide. An advantage is that the curved distal end can provide minimally invasive separation of tissue adjacent to the bone. One possible advantage is that the curved distal end can be closer to the bone during circumvention. Another possible advantage is that the curved distal end is inserted with a smaller incision. In some embodiments, the curved distal end is blunt.

In some embodiments, the curved distal end is blunt. In some embodiments, the curved distal end is pointed or sharpened. In some embodiments, the curved distal end can have a severe point. In some embodiments, the curved distal end has a low profile configuration. An advantage is that the curved distal end can separate tissue or muscle from the bone during movement. An advantage is that the curved distal end can be inserted into a small space between bones and surrounding anatomical features. In some embodiments, the curved distal end has a flattened surface. An advantage is that the flattened surface of the curved distal end can lie flat against the bone surface. In some embodiments, the curved distal end is shaped to pass the curved distal end through the linea aspera on the femur. In some embodiments, the curved distal end is shaped to pass the curved distal end through tissue or muscles. In some embodiments, the curved distal end is not able to penetrate bone. In some embodiments, the curved distal end is not able to penetrate an artery.

In some embodiments, the distal end of the device is curved to be passed around the bone. In some embodiments, the curved distal end is passed around the bone before the wire or cable is inserted into the flexible tube. In some embodiments, the curved distal end is passed around the bone after the wire or cable is inserted into the flexible tube. In some embodiments, the wire or cable provides rigidity to the flexible tube. In some embodiments, the curved distal end is passed around the bone and the wire is inserted in the other end of the device.

In some embodiments, the flexible tube has a length longer than the curved distal end and/or the appendage guide. In some embodiments, the flexible tube extends in the opposite direction as the curved distal end. An advantage is that the flexible tube extends beyond the appendage guide. In some embodiments, the flexible tube is straight. An advantage is that the flexible tube can prevent or limit tangles of the wire and/or cable. In some embodiments, the flexible tube is curved. In some embodiments, the flexible tube houses the entire length of the cable or wire. In some embodiments, the cable or wire extends from an end of the flexible tube. In some embodiments, the tube is flexible to allow the tube to be placed anywhere relative to the incision. In some embodiments, the tube is flexible to allow the tube to be placed anywhere external to the patient. An advantage is that the flexible tube can remain external or mostly external to the patient during surgery. In some embodiments, the flexible tube has a flattened surface. An advantage is that the flattened surface of the flexible tube can lie flat against the bone surface.

In some embodiments, the flexible tube and the curved distal end form a continuous channel. In some embodiments, the flexible tube and the curved distal end form a channel with a straight portion and a curved portion. In some embodiments, the flexible tube and the curved distal end form a smooth channel. An advantage is that the wire and/or cable can pass easily from the flexible tube to the curved distal end. In some embodiments, the device includes two flexible tubes and two curved distal ends. In some embodiments, each flexible tube and corresponding curved distal end forms a continuous channel. In some embodiments, the device includes two separate channels. In some embodiments, the device includes two or more separate channels.

In some embodiments, the curved distal end includes a slot that intersects the channel. Some embodiments can include the following advantages: the flexible tube can slide past the slot; the wire and/or cable can slide past the slot; the wire and/or cable cannot pass through the slot; the appendage guide and the curved distal end can flex relative to each other; the appendage guide and the curved distal end can form a hinge; and/or the appendage guide can pivot relative to the curved distal end. In some embodiments, the flexible tube and the curved distal end include a region of reduced thickness that intersects the channel. One advantage is that the curved distal end can pivot or articulate. Another advantage is that the flexible tube and the curved distal end can be linked via a hinge. Yet another advantage is that the appendage guide can change the direction of the application of force relative to the curved distal end. A further advantage is that the device can include a low-profile hinge.

In some embodiments, the wire and/or cable is passed below the finger of the user. In some embodiments, the wire/cable is passed along the palm. In some embodiments, the wire/cable is passed opposite the nail of the finger of the user. An advantage is that the wire can have a smoother transition from the tube to the curved distal end. An advantage is that the wire can have a shorter distance from the tube to the curved distal end. Another advantage is that the appendage guide is unobstructed. In some embodiments, the wire or cable is passed distally and downwardly. In some embodiments, the wire or cable is passed in front of the finger of the user.

In some embodiments, the device allows two separate cables or wires to be passed. In some embodiments, the device allows two separate cables or wires to be passed simultaneously. In some embodiments, the device allows two separate cables or wires to be passed independently. In some embodiments, the device allows two different cables or wires to be passed (e.g., different dimensions, uses, etc.). In some embodiments, the device allows two similar or identical cables or wires to be passed. In some embodiments, each cable or wire is passed in a separate channel or lumen. In some embodiments, the device includes a dual lumen shaft. In some embodiments, the device includes two separate flexible tubes or channels. An advantage is that the wire or cable in separate flexible tubes can reduce tangles of the wire or cable. In some embodiments, two or more cables or wires are passed in the same channel or lumen.

In some embodiments, the appendage guide and the curved distal end are formed of the same material. In some embodiments, the appendage guide and the curved distal end are formed of different materials. In some embodiments, the tube and the curved distal end are formed of the same material. In some embodiments, the tube and the curved distal end are formed of different materials. In some embodiments, the appendage guide and the flexible tube are formed of the same material. In some embodiments, the appendage guide and the flexible tube are formed of different materials. In some embodiments, the appendage guide and/or the curved distal end and/or the tube are formed of metal (e.g., titanium, stainless steel, etc.). In some embodiments, the appendage guide and/or the curved distal end and/or the tube are formed of plastic (e.g., PEEK, HDPE, etc.).

In some embodiments, the device is a wire passer. In some embodiments, the device is a cerclage wire passer. In some embodiments, the device is an orthopedic wire passer. In some embodiments, the device is a 45 mm wire passer. In some embodiments, the device is a large cable passer. In some embodiments, the device is a bone fixation wire passer. In some embodiments, the device is a universal wire passer.

In some embodiments, the cerclage wire/cable passing device can preferably be made of a flexible, sterilizable material that could be disposed of, making the device "one use only." In other embodiments, the device can be made of, for example, a metal or other suitable material to allow for re-sterilization.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning a cerclage passer device adjacent a bone" includes "instructing the positioning of a cerclage passer device adjacent a bone." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A cerclage wire or cable passer comprising:
a flexible tube comprising a first surface and a second surface opposite the first surface, wherein the first surface is substantially flat and configured to contact an outer surface of a bone and lie against the bone as it is passed around the bone, the flexible tube further comprising a proximal end, a distal end, a lumen configured to house a wire or cable therethrough, and a elongate body therebetween, the distal end comprising a curved shape; and
an appendage guide comprising an open proximal end and a closed distal end, the appendage guide directly adjacent the second surface of the flexible tube, the appendage guide configured to house the distal phalanx of a finger of an operator, the distal end of the appendage guide defining a transition from the elongate body of the flexible tube to the curved distal end of the flexible tube extending distally past the distal end of the appendage guide.

2. The cerclage passer of claim 1, configured to be sufficiently flexible to conform to the radius of curvature of the bone from pressure from the finger.

3. The cerclage passer of claim 1, wherein the appendage guide comprises a smooth surface.

4. The cerclage passer of claim 1, wherein the appendage guide is configured to allow passage of the guide through tissue, and sized to hold the distal phalanx of the finger securely and allow tactile appreciation for a location of the curved distal end of the flexible tube.

5. The cerclage passer of claim 1, wherein the distal end of the flexible tube comprises a constant radius of curvature.

6. The cerclage passer of claim 1, wherein the distal end of the flexible tube comprises a variable radius of curvature.

7. The cerclage passer of claim 1, wherein the flexible tube has a length sufficient that the finger in the appendage guide does not completely encircle the bone, to allow retrograde passage of the wire/cable.

8. The cerclage passer of claim 1, wherein the flexible tube is of sufficient rigidity that the guiding finger can discern the position of the curved distal end of the flexible tube against the bone by friction, preventing soft tissue interposition between the cerclage passer and the bone.

9. The cerclage passer of claim 1, wherein the appendage guide comprises a clip.

10. The cerclage passer of claim 1, wherein the flexible tube comprises a rectangular cross-section.

11. The cerclage passer of claim 1, wherein the flexible tube comprises a square cross-section.

12. The cerclage passer of claim 1, wherein the flexible tube comprises a semi-circular cross-section.

13. The cerclage passer of claim 1, further comprising a hinge.

14. The cerclage passer of claim 1, wherein the appendage guide comprises a slot to increase flexibility of the appendage guide.

15. The cerclage passer of claim 1, wherein the appendage guide comprises an area of reduced thickness to increase flexibility of the appendage guide.

16. The cerclage passer of claim 1, wherein the flexible tube comprises a slot to increase flexibility of the flexible tube.

17. A cerclage passing system configured to pass multiple wires around a bone simultaneously, comprising:
a first cerclage passer as in claim 1,
a second cerclage passer as in claim 1,
wherein the first cerclage passer and the second cerclage passer are attached via a connector positioned proximal to the appendage guides of the first cerclage passer and the second cerclage passer.

18. The cerclage passing system of claim 17, wherein the first cerclage passer and the second cerclage passer are permanently attached via the connector.

19. The cerclage passing system of claim 17, wherein the first cerclage passer and the second cerclage passer are removably attachable via the connector.

20. A method of passing a tether around a bone, comprising:
providing a first cerclage passer as in claim 1;
providing a second cerclage passer as in claim 1;
connecting the first cerclage passer to the second cerclage passer in parallel;
placing a first finger into the appendage guide of the first cerclage passer;
placing a second finger into the appendage guide of the second cerclage passer;
passing the first cerclage passer and the second cerclage passer directly adjacent to and circumferentially around an outer surface of the bone;
passing a first tether through the lumen of the first cerclage passer;
passing a second tether through the lumen of the second cerclage passer; and
withdrawing the first and second cerclage passers, thereby placing the first tether and the second tether at a desired distance from each other and around the bone.

21. The method of claim 20, further comprising connecting a third cerclage passer to the first cerclage passer and the second cerclage passer in parallel.

* * * * *